United States Patent
Nakahara

(10) Patent No.: US 11,409,088 B2
(45) Date of Patent: Aug. 9, 2022

(54) OPTICAL SYSTEM

(71) Applicant: CANON KABUSHIKI KAISHA, Tokyo (JP)

(72) Inventor: Seiji Nakahara, Sakura (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 370 days.

(21) Appl. No.: 16/779,890

(22) Filed: Feb. 3, 2020

(65) Prior Publication Data
US 2020/0257097 A1 Aug. 13, 2020

(30) Foreign Application Priority Data
Feb. 8, 2019 (JP) .............................. JP2019-021195

(51) Int. Cl.
| | | |
|---|---|---|
| G01R 33/28 | (2006.01) | |
| G02B 17/08 | (2006.01) | |
| G02B 3/08 | (2006.01) | |
| G01R 33/30 | (2006.01) | |
| A61B 6/03 | (2006.01) | |
| A61B 5/055 | (2006.01) | |

(52) U.S. Cl.
CPC .............. *G02B 17/08* (2013.01); *A61B 5/055* (2013.01); *A61B 6/032* (2013.01); *G01R 33/283* (2013.01); *G01R 33/307* (2013.01); *G02B 3/08* (2013.01)

(58) Field of Classification Search
CPC .......... G02B 17/08; G02B 3/08; A61B 5/055; A61B 6/032; A61B 6/03; A61B 6/0407; A61B 5/742; A61B 5/704; G01R 33/283; G01R 33/307
See application file for complete search history.

(56) References Cited

U.S. PATENT DOCUMENTS

| | | | |
|---|---|---|---|
| 4,512,631 A * | 4/1985 | VanBreemen | G03B 21/625 348/E5.138 |
| 8,964,111 B2 | 2/2015 | Nakahara | |
| 2016/0037090 A1 | 2/2016 | Nakahara | |
| 2020/0289075 A1* | 9/2020 | Anderson | A61B 6/032 |

FOREIGN PATENT DOCUMENTS

| | | |
|---|---|---|
| JP | 2006084904 A | 3/2006 |
| JP | 2006126526 A | 5/2006 |
| JP | 2013213884 A | 10/2013 |
| JP | 2016202514 A | 12/2016 |

* cited by examiner

*Primary Examiner* — G. M. A Hyder

(74) *Attorney, Agent, or Firm* — Carter, DeLuca & Farrell LLP

(57) ABSTRACT

In order to provide an optical system to be installed in a projection system which is capable of allowing a patient to view a clear image in a diagnostic imaging apparatus, the optical system according to the present invention includes a Fresnel lens having a base material and a plurality of annular sections arranged around a center axis on a reference surface of the base material, and a deflection element configured to deflect light from the Fresnel lens. In a cross section including the center axis, an inclination angle of the annular sections to the reference surface changes asymmetrically between from a middle point of one and other ends of the Fresnel lens to the one end and from the middle point to the other end.

15 Claims, 11 Drawing Sheets

OPTICAL SYSTEM

BACKGROUND OF THE INVENTION

Field of the Invention

The present invention relates to an optical system and is preferably applicable to a projection system provided in a diagnostic imaging apparatus, for example.

Description of the Related Art

Heretofore, with a diagnostic imaging apparatus using a technique such as computer tomography (CT) or magnetic resonance imaging (MRI), some patients experience a feeling of pressure or a feeling of confinement inside the inspection space (bore) during diagnosis.

Japanese Patent Application Laid-open No. 2016-202514 discloses a diagnostic imaging apparatus including a projection system that projects an image on a projected surface inside the bore in the diagnostic imaging apparatus and allows a patient to view the image on the projected surface via a reflection member, in order to alleviate the feeling of pressure or the feeling of confinement experienced by the patient.

However, in the diagnostic imaging apparatus disclosed in Japanese Patent Application Laid-open No. 2016-202514, a lower portion of the image displayed on the projected surface by the projection system, which is to be viewed by the patient via the reflection member, does not have sufficient brightness, so that the difference in brightness between the upper and lower portions of the image is large, which renders the image unclear.

In view of the above, an object of the present invention is to provide an optical system to be installed in a projection system which is capable of allowing a patient to view a clear image in a diagnostic imaging apparatus.

SUMMARY OF THE INVENTION

An optical system according to the present invention includes a Fresnel lens having a base material and a plurality of annular sections arranged around a center axis on a reference surface of the base material, and a deflection element configured to deflect light from the Fresnel lens. In a cross section including the center axis, an inclination angle of the annular sections to the reference surface changes asymmetrically between from a middle point of one and other ends of the Fresnel lens to the one end and from the middle point to the other end.

Further features of the present invention will become apparent from the following description of exemplary embodiments with reference to the attached drawings.

DESCRIPTION OF THE EMBODIMENTS

An inspection system including an optical system according to an embodiment will be described below in detail with reference to the accompanying drawings. Note that the drawings presented below may be depicted with different scales from the actual ones in order to facilitate understanding of the embodiment.

Figure 1:
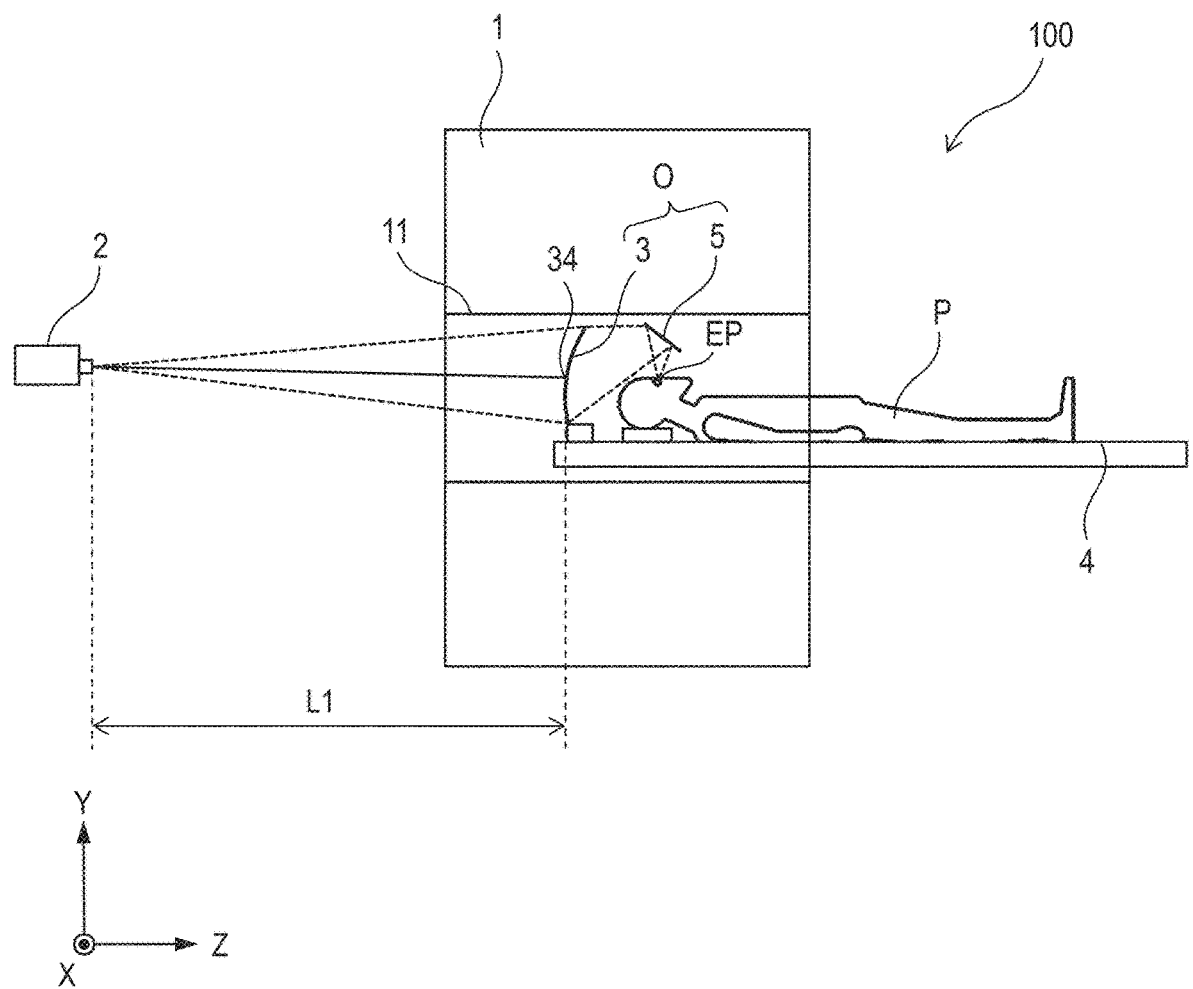
FIG. 1 is a schematic cross-sectional view of an inspection system in a diagnostic mode provided with a projection system including an optical system according to an embodiment of the present invention.

FIG. 1 illustrates a schematic cross-sectional view of an inspection system (diagnostic imaging system) 100 in a diagnostic mode (first mode) provided with a projection system including an optical system O according to the embodiment.

Note that in the following, a direction perpendicular to a table 4, i.e., vertical direction, is a Y direction (first direction), a direction perpendicular to the exit surface of the projection lens of a projector 2 is a Z direction (second direction), and a direction perpendicular to the Y direction and the Z direction is an X direction.

Also, a direction from the table 4 toward a mirror 5 is a +Y direction, and a direction from the projector 2 toward a patient (subject) P is a +Z direction.

Here, an MRI apparatus is used as the inspection system 100, for example. Alternatively, the inspection system 100 may be an apparatus using a different technique from MRI such as CT.

The MRI apparatus used as the inspection system 100 is an apparatus that obtains tomographic images of a patient in a non-invasive manner by using resonance.

To obtain tomographic images of a patient P in the MRI apparatus 100, the patient P is placed inside a substantially hollow, elongated bore 1 having electromagnetic coils.

In particular, as illustrated in FIG. 1, to obtain tomographic images of the head of the patient P, the head of the patient P is placed in a substantially center portion of the bore 1.

The inspection system 100 includes the bore 1, the projector 2 (projection unit), a screen 3 (optical element), the table (bed) 4, and the mirror 5 (reflection element, deflection element).

Here, the optical system O according to the embodiment consists of the screen 3 and the mirror 5, and the projection system including the optical system O according to the embodiment consists of the projector 2, the screen 3, and the mirror 5.

The screen 3 is fixed at the placement surface of the table 4, which is parallel to a Z-X plane, by being fitted in a groove portion not illustrated which is provided in the table 4, for example.

Also, the mirror 5 is movably supported in the bore 1 by a supporting unit not illustrated and is disposed between the screen 3 and the focal point of the optical system O (first focal point) along the optical path of video light emitted from the projector 2.

The projector 2 has a display element (image display element) not illustrated that has a display surface, an optical system not illustrated (projection optical system) that projects an image displayed on the display surface, and so on. Meanwhile, a liquid crystal panel (spatial modulator), a digital mirror device (DMD), or the like can be employed as the display element.

In the inspection system 100, as illustrated in FIG. 1, video light emitted from the projector 2 is incident on the screen 3, so that a video is projected on the screen 3.

Figure 5:
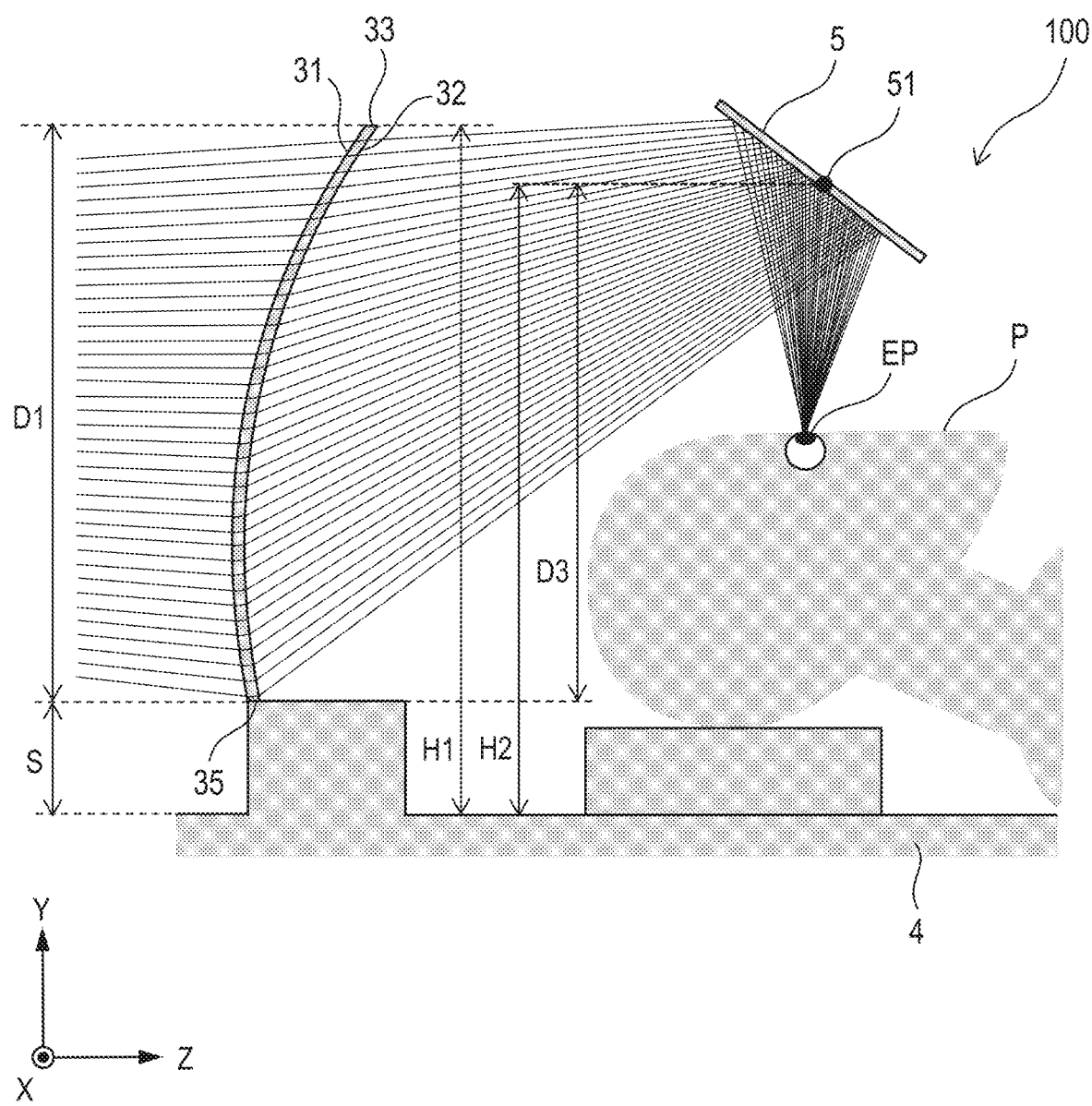
FIG. 5 is a partially enlarged cross-sectional view of the inspection system around the optical system according to the embodiment.

A Fresnel lens 31 on which a plurality of unit lenses are arranged side by side is formed on the incident surface at the projector 2 side (first optical surface) of the screen 3 according to the embodiment, and a diffusion surface 32 is formed on the exit surface at the patient P side (second optical surface) of the screen 3 (see FIG. 5).

Note that the Fresnel lens 31 may be directly formed on the surface of the screen 3 or a sheet on which the Fresnel lens 31 is formed may be attached to the surface of the screen 3.

Also, the diffusion surface 32 may be directly formed on the surface of the screen 3 or a sheet on which the diffusion surface 32 is formed may be attached to the surface of the screen 3.

Meanwhile, the incident surface and the exit surface of the screen 3 according to the embodiment are formed as a convex surface and a concave surface, respectively.

Video light emitted from the projector 2 is refracted by the Fresnel lens 31 on the screen 3 and then diffused by the diffusion surface 32.

Thereafter, part of the video light diffused by the diffusion surface 32 is reflected by the mirror 5 and reaches an eye point EP on the patient P.

In other words, the patient P can view a video projected on the screen 3 through the mirror 5 while lying on his or her back on the table 4.

Here, the focal point (first focal point) of the optical system O, consists of the screen 3 and the mirror 5, is set so as to correspond to the position of the eye point EP on the patient P.

Note that in the inspection system 100, part of the video light diffused by the diffusion surface 32 may be caused to reach the eye point EP on the patient P by using a prism or the like in place of the mirror 5.

It is also possible that part of the video light emitted from the projector 2 is not made incident on the screen 3 but is made incident directly on an inner wall 11 of the bore 1 to thereby project a video on the inner wall 11 of the bore 1.

In this way, the patient P can view the video on a larger area than the screen 3, which facilitates removal of the feeling of pressure and the feeling of tension which the patient P experiences by being inside the bore 1.

Also, forming the Fresnel lens 31 on the incident surface of the screen 3 brings about an advantageous effect of making the annular sections on the Fresnel lens 31 less visible to the patient P.

Figure 2:
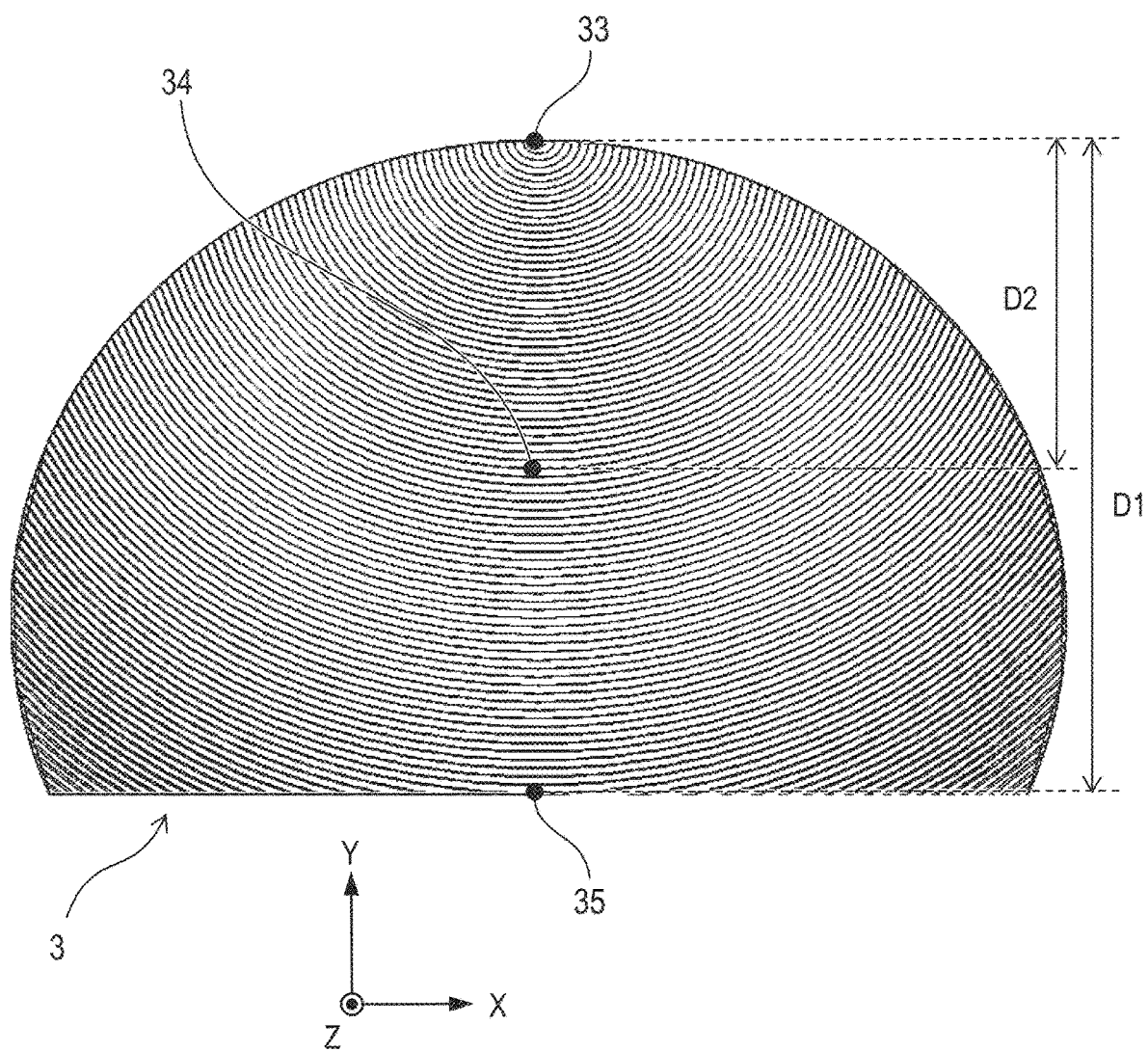
FIG. 2 is a schematic view of a Fresnel lens formed on an incident surface of a screen according to the embodiment as seen from a projector side.

FIG. 2 is a schematic view of the Fresnel lens 31, which is formed on the incident surface of the screen 3 according to the embodiment, as seen from the projector 2 side.

As illustrated in FIG. 2, the Fresnel lens 31 on the screen 3 according to the embodiment includes a plurality of unit lenses arranged side by side in circular and substantially arc shapes over the entire incident surface of the screen 3.

In other words, on the incident surface of the screen 3 according to the embodiment are formed a plurality of annular sections arranged side by side about a center axis as the center.

Figure 4:
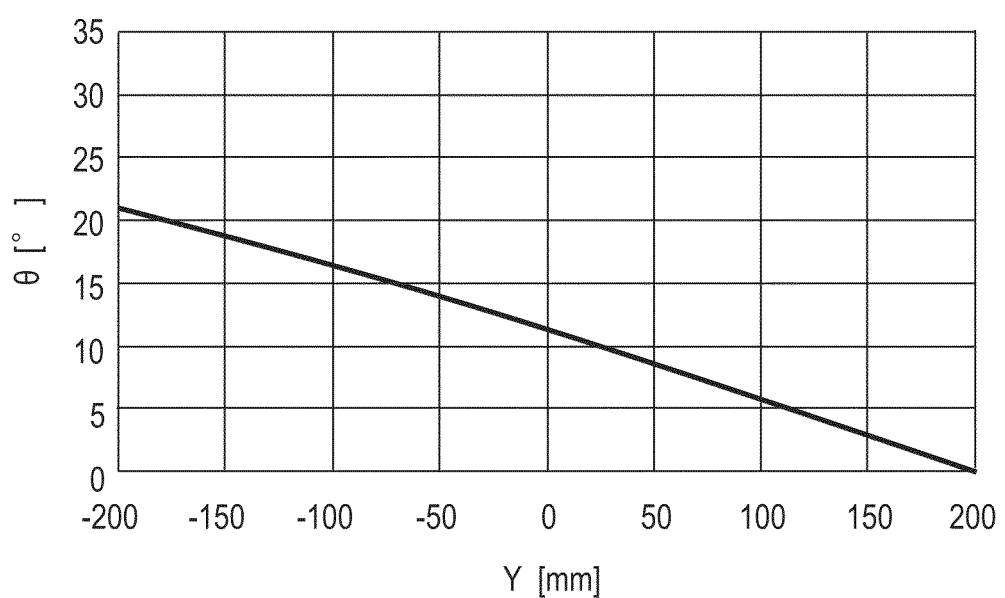
FIG. 4 is a diagram illustrating the distribution of the inclination angle of unit lenses on the screen according to Numerical Example 1 of the embodiment.

Note that the Fresnel lens 31 does not have to be formed on the entire incident surface of the screen 3 according to the embodiment. In particular, the Fresnel lens 31 does not have to be formed on an upper portion of the incident surface of the screen 3 where an inclination angle θ is small, as illustrated in FIG. 4 to be mentioned later.

Also, the center of the circular and substantially arc portions will hereinafter be referred to as a center (annular section center, center axis) 33 of the Fresnel lens 31. Note that on the screen 3 according to the embodiment, the center 33 of the Fresnel lens 31 coincides with an upper end 33 of the Fresnel lens 31 in the Y direction.

In other words, on the Fresnel lens 31 on the screen 3 according to the embodiment, the plurality of unit lenses are arranged side by side in circular and substantially arc shapes about the center axis 33 extending through an upper end 33 of the incident surface of the screen 3.

Note that in the embodiment, the upper end 33 of the incident surface of the screen 3 and the center 33 of the Fresnel lens 31 do not have to coincide with each other.

Also, the center axis of the Fresnel lens 31 is parallel to a surface normal to the incident surface of the screen 3 at the position of the center 33.

Alternatively, the Fresnel lens 31 may be formed by arranging a plurality of unit lenses side by side in a linear pattern.

Meanwhile, the center of the projection area on the screen 3 by the projector 2 is set so as to correspond to a middle point (profile center) 34 on the screen 3.

Note that the center of the projection area on the screen 3 by the projector 2 may be shifted in the +Y direction from the middle point 34 on the screen 3 in view of the fact that the part of video light emitted from the projector 2 may be made incident directly on the inner wall 11 of the bore 1 to project a video on the inner wall 11 of the bore 1.

Also, as illustrated in FIG. 2, the screen 3 has what is called a semicircular shape having an installation surface parallel to a Z-X cross section (a first surface perpendicular to a Y-Z cross section including the center axis of the Fresnel lens 31).

This improves the stability of the screen 3, enabling easy installation of the screen 3 on the table 4, easy hold of the screen 3 by the table 4, and the like.

Figure 3:
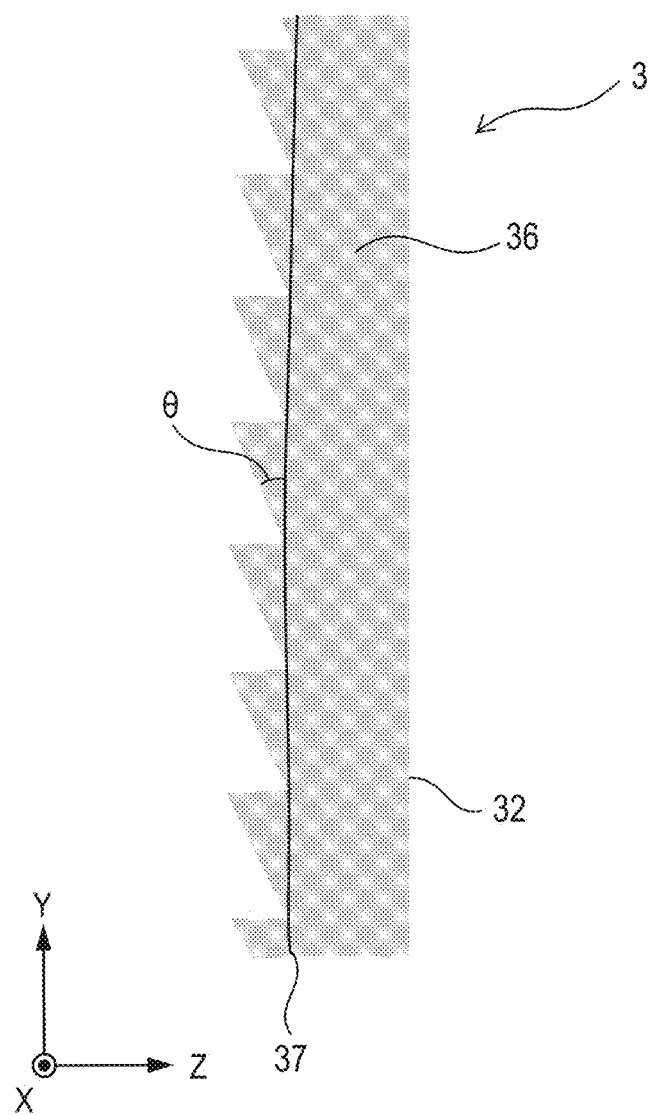
FIG. 3 is a partially enlarged cross-sectional view of the screen according to the embodiment.

FIG. 3 illustrates a partially enlarged cross-sectional view of the screen 3 according to the embodiment.

Here, in the Fresnel lens 31, which is formed on the screen 3 according to the embodiment, the inclination angle of each unit lens in a Y-Z cross section (first cross section) to a surface (reference surface) 37 of a base member 36 is defined as θ. Note that θ>0 holds when the Y component of a normal to the lens surface of the unit lens is oriented in a −Y direction.

Note also that the annular sections formed of the unit lenses of the Fresnel lens 31 each consists of an annular section surface (inclined surface) that contributes to imaging of an effective light flux and an annular section wall surface (side surface) that does not contribute to the imaging of the effective light flux, and the inclination angle θ of the annular section can be defined as the angle (acute angle) of the annular section surface to the surface 37 of the base member 36.

In the screen 3 according to the embodiment, the surface 37 of the base member 36 is formed in a dome shape having curvature. The inclination angle θ of each unit lens is therefore, but not limited to, an inclination angle to the curved surface 37 of the base material 36. The surface 37 of the base member 36 may be formed as a flat surface.

FIG. 4 illustrates the distribution of the inclination angle θ of the unit lenses in the Fresnel lens 31 formed on the screen 3 according to Numerical Example 1 of the embodiment.

Here, the horizontal axis of FIG. 4 represents Y coordinates on the Fresnel lens 31 with an origin corresponding to the middle point 34 between the upper end 33 of the Fresnel lens 31 in the Y direction and a lower end 35 of the Fresnel lens 31 at the same X coordinate as that of the upper end 33.

The above-mentioned upper end 33 and lower end 35 are one end and the other end in a cross section of Fresnel lens 31 including its center axis and are the end farther from the table 4 and the end closer to the table 4 in the state where the screen 3 is installed in the inspection system 100, respectively.

As illustrated in FIG. 4, in the screen 3 according to Numerical Example 1 of the embodiment, the distribution (change) of the inclination angle θ of the unit lenses is asymmetrical about the middle point 34 in the Y direction. Specifically, the inclination angle θ is larger at a lower (−Y direction) portion of the screen 3 than at an upper (+Y direction) portion of the screen 3. That is, the inclination angle θ changes asymmetrically between from the middle point 34 of both ends to the upper end 33 and from the middle point 34 to the lower end 35.

In other words, in the screen 3 according to Numerical Example 1 of the embodiment, the position of the center 33 of the Fresnel lens 31 and the position of the middle point 34 on the screen 3 are different from each other.

Thus, video light incident on the lower portion of the screen 3 is guided to the eye point EP on the patient P. This increases the brightness at the lower portion of the screen 3 and accordingly decreases the difference in brightness between the upper portion and the lower portion of the screen 3.

As illustrated in FIG. 2, the upper end 33, which is the center of the circular and substantially arc portions of the Fresnel lens 31, is disposed on the side opposite to the table 4 (+Y side) relative to the middle point 34 whereas the lower end 35 of the Fresnel lens 31 is disposed on the same side as the table 4 relative to the middle point 34 (−Y side).

Here, the screen 3 according to the embodiment preferably satisfies the following condition:

$$0.2 < D2/D1 < 0.8 \tag{1},$$

where D1 is the distance in the Y direction from the upper end 33 of the incident surface of the screen 3 to the lower end 35 at the same X coordinate as that of the upper end 33, and D2 is the distance in the Y direction from the center 33 of the Fresnel lens 31 to the middle point 34.

Satisfying the conditional expression (1) enables the Fresnel lens 31 to refract whole video light incident on the screen 3 in the +Y direction. This increases the brightness at the lower portion of the screen 3 and therefore facilitates correction of the difference in brightness between the upper portion and the lower portion of the screen 3.

If the ratio falls below the lower limit value in the conditional expression (1), it will be difficult to guide video light incident on the lower portion of the screen 3 to the eye point EP on the patient P. As a result, the lower portion of the screen 3 appears dark.

On the other hand, if the ratio exceeds the upper limit value in the conditional expression (1), it will be difficult to guide video light incident on the upper portion of the screen 3 to the eye point EP on the patient P. As a result, the upper portion of the screen 3 appears dark.

Note that the screen 3 according to the embodiment more preferably satisfies the conditional expression (1a) given below:

$$0.3 < D2/D1 < 0.6 \tag{1a}.$$

FIG. 5 illustrates a partially enlarged cross-sectional view of the inspection system 100 around the optical system O according to the embodiment.

As illustrated in FIG. 5, video light emitted from the projector 2 is refracted by the Fresnel lens 31 on the screen 3 and then diffused by the diffusion surface 32.

Thereafter, part of the video light diffused by the diffusion surface 32 is reflected by the mirror 5 and reaches the eye point EP on the patient P.

Here, the screen 3 according to the embodiment preferably satisfies the following condition:

$$0.8 < H2/H1 < 1.2 \tag{2},$$

where H1 is the distance in the Y direction from the table 4 to the center 33 of the Fresnel lens 31, and H2 is the distance in the Y direction from the table 4 to a center 51 of the reflection surface (deflection surface) of the mirror 5.

The conditional expression (2) defines a relation between the height from the table 4 to the center 33 of the concentric circular and substantially arc portions of the Fresnel lens 31 and the height from the table 4 to the center 51 of the reflection surface of the mirror 5.

If the ratio exceeds the upper limit value in the conditional expression (2) or falls below the lower limit value in the conditional expression (2), it will be difficult to guide video light incident on the screen 3 to the eye point EP on the patient P and it will thus be difficult to correct the brightness of a video displayed on the screen 3.

Note that the screen 3 according to the embodiment more preferably satisfies the conditional expression (2a) given below:

$$0.8 < H2/H1 < 1.0 \quad (2a).$$

Also, the screen 3 according to the embodiment preferably satisfies the conditional expression (2') given below and more preferably satisfies the conditional expression (2a') given below:

$$0.8 < (H2-S)/(H1-S) < 1.2 \quad (2'), \text{ and}$$

$$0.8 < (H2-S)/(H1-S) < 1.0 \quad (2a'),$$

where S is the distance in the Y direction from the table 4 to the lower end 35 of the screen 3.

Here, with H1−S=D1 and H2−S=D3, the conditional expressions (2') and (2a') can be rewritten as the conditional expressions (3) and (3a) given below, respectively:

$$0.8 < D3/D1 < 1.2 \quad (3), \text{ and}$$

$$0.8 < D3/D1 < 1.0 \quad (3a).$$

Figure 6:
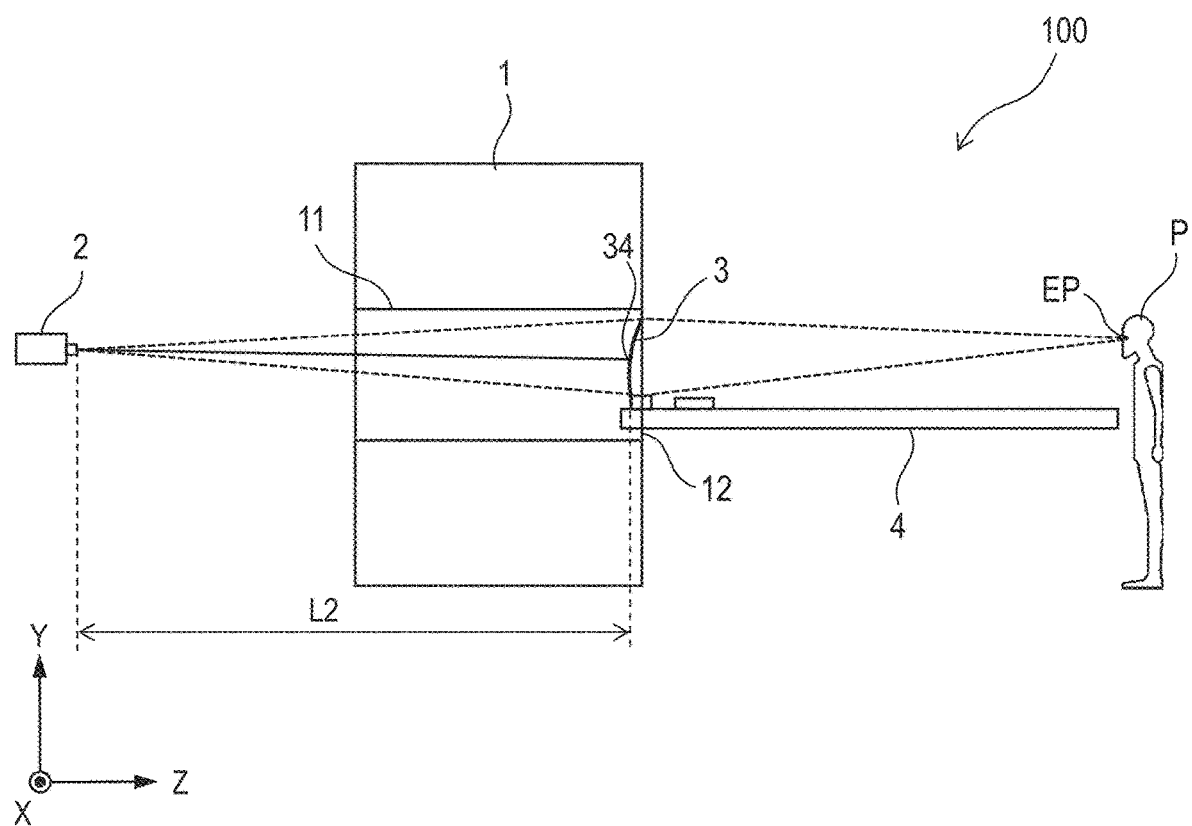
FIG. 6 is a schematic cross-sectional view of the inspection system in a preparation mode, which is provided with the projection system including the optical system according to the embodiment.

FIG. 6 illustrates a schematic cross-sectional view of the inspection system 100 in a preparation mode (second mode), which is provided with the projection system including the optical system O according to the embodiment.

As illustrated in FIG. 6, when the inspection system 100 is in the preparation mode, the movable table 4 is moved in the Z direction such that the screen 3 is disposed at the position of an opening 12 formed at the end of the bore 1 in the +Z direction.

Video light emitted from the projector 2 is refracted by the Fresnel lens 31 on the screen 3 and then diffused by the diffusion surface 32, and the diffused video light reaches the eye point EP on the patient P.

Thus, by viewing a video displayed on the screen 3, the patient P can eliminate the anxiety which he or she experiences before entering the narrow space inside the bore 1.

Also, as illustrated in FIG. 6, when the inspection system 100 is in the preparation mode, the mirror 5 is not disposed within the optical path from the projector 2 to the eye point EP on the patient P. In other words, the mirror 5 is not disposed between the screen 3 and the focal point of the optical system (second focal point) along the optical path of video light emitted from the projector 2.

Here, assume that the distance along the Z axis from the projection lens of the projector 2 to the middle point 34 on the incident surface of the screen 3 when the inspection system 100 is in the diagnostic mode illustrated in FIG. 1 is L1. Also, assume that the distance along the Z axis from the projection lens of the projector 2 to the middle point 34 on the incident surface of the screen 3 when the inspection system 100 is in the preparation mode illustrated in FIG. 6 is L2.

Further, the distance from the screen 3 to the point of condensation of parallel light wider than the area of the Fresnel lens 31 on the screen 3 (e.g., sunlight) exiting from the screen 3 after entering the Fresnel lens 31 is defined as a focal length f. Furthermore, the above-mentioned condensation point is defined as the focal point of the optical system O of the inspection system 100.

With these definitions, the inspection system 100, which is provided with the projection system including the optical system O according to the embodiment, preferably satisfies the following conditions:

$$0.35 < f/L1 < 1.26 \quad (4), \text{ and}$$

$$0.24 < f/L2 < 0.83 \quad (5).$$

Satisfying the conditional expression (4) increases the brightness at the lower portion of the screen 3 when the inspection system 100 is in the diagnostic mode, and therefore facilitates correction of the difference in brightness between the upper portion and the lower portion of the screen 3.

If the focal length f is so short that the ratio falls below the lower limit value in the conditional expression (4), it will be difficult to guide video light incident on the screen 3 to the eye point EP on the patient P during the diagnostic mode. As a result, the video appears dark.

On the other hand, if the ratio exceeds the upper limit value in the conditional expression (4), the brightness correction effect by the Fresnel lens 31 will be insufficient. This will result in an insufficient correction of the difference in brightness between the upper portion and the lower portion of the screen 3.

Also, by satisfying the conditional expression (5), the inspection system 100 can easily maintain a uniform distribution of light amount on the screen 3 during the preparation mode.

If the focal length is so short that the ratio falls below the lower limit value in the conditional expression (5), it will be difficult to guide video light incident on the screen 3 to the eye point EP on the patient P during the preparation mode. As a result, the video appears dark.

Note that the inspection system 100, which is provided with the projection system including the optical system O according to the embodiment, more preferably satisfies the conditional expressions (4a) and (5a) given below:

$$0.50 < f/L1 < 1.10 \quad (4a), \text{ and}$$

$$0.30 < f/L2 < 0.72 \quad (5a).$$

Table 3 below lists specification values of the inspection system 100 according to Numerical Example 1 of the embodiment.

As described in Table 3, the inspection system 100 according to Numerical Example 1 of the embodiment satisfies each conditional expression.

Figure 7A:
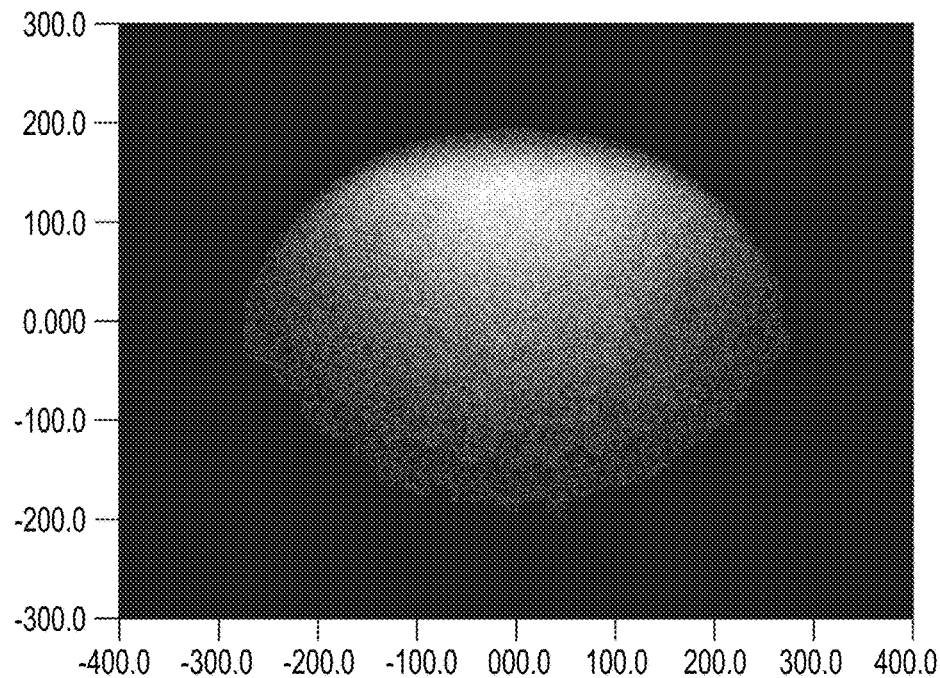
FIG. 7A is a diagram illustrating the distribution of light amount on a screen in an inspection system of a conventional example in the diagnostic mode.
Figure 7B:
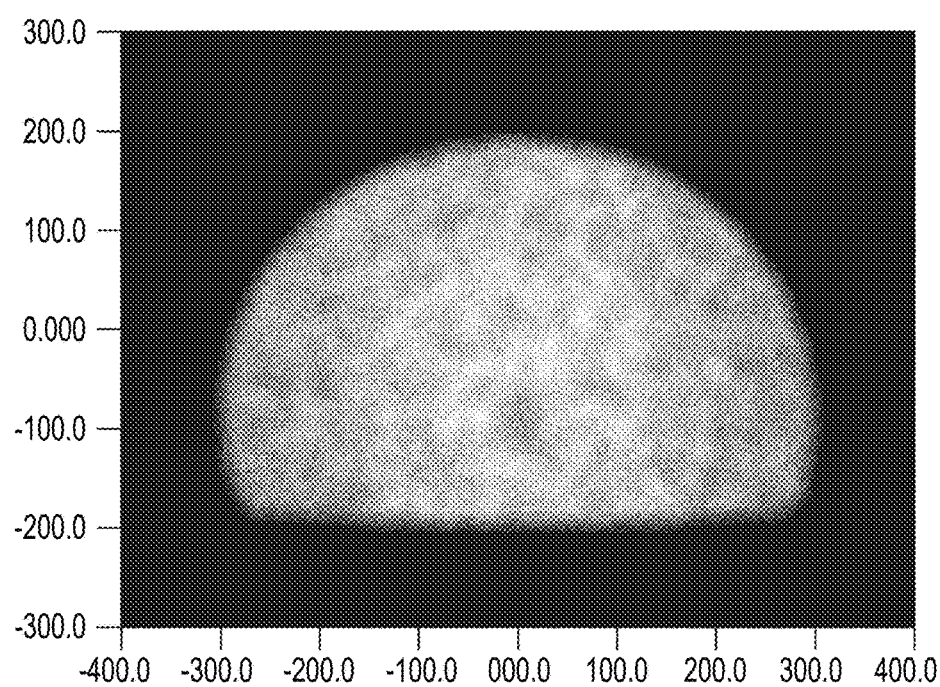
FIG. 7B is a diagram illustrating the distribution of light amount on the screen in the inspection system of the conventional example in the preparation mode.

FIGS. 7A and 7B are diagrams illustrating the distributions of amount of light on a screen 3 in an inspection system of a conventional example in the diagnostic mode and the preparation mode, respectively, the light being video light to be incident on the eye point EP.

Here, the inspection system of the conventional example has the same configuration as the inspection system 100 except that the incident surface of the screen 3 is a transmission surface without the Fresnel lens 31 formed thereon.

Also, the coordinates of the middle point 34 on the incident surface (Fresnel surface) of the screen 3, the center of the exit surface of the projection lens of the projector 2, the center 51 of the reflection surface of the mirror 5, and the eye point EP during the diagnostic mode are as listed in Table 1 below.

TABLE 1

| Diagnostic Mode | X Coordinate | Y Coordinate | Z Coordinate |
|---|---|---|---|
| Middle Point 34 on Incident Surface of Screen 3 | 0 | 0 | 0 |

TABLE 1-continued

| Diagnostic Mode | X Coordinate | Y Coordinate | Z Coordinate |
|---|---|---|---|
| Center of Exit Surface of Projection Lens of Projector 2 | 0 | 0 | −1900 |
| Center 51 of Reflection Surface of Mirror 5 | 0 | 156 | 388 |
| Eye Point EP | 0 | −14 | 379 |

Also, the coordinates of the middle point 34 on the incident surface (Fresnel surface) of the screen 3, the center of the exit surface of the projection lens of the projector 2, and the eye point EP during the preparation mode are as listed in Table 2 below.

TABLE 2

| Preparation mode | X coordinate | Y coordinate | Z coordinate |
|---|---|---|---|
| Middle point 34 on incident surface of screen 3 | 0 | 0 | 0 |
| Center of exit surface of projection lens of projector 2 | 0 | 0 | −2900 |
| Eye point EP | 0 | 95 | 2576 |

In the inspection system of the conventional example, as illustrated in FIG. 7A in particular, the difference in brightness between the upper portion and the lower portion of the screen 3 during the diagnostic mode is large, and the video in the lower portion in particular is dark.

Figure 8A:
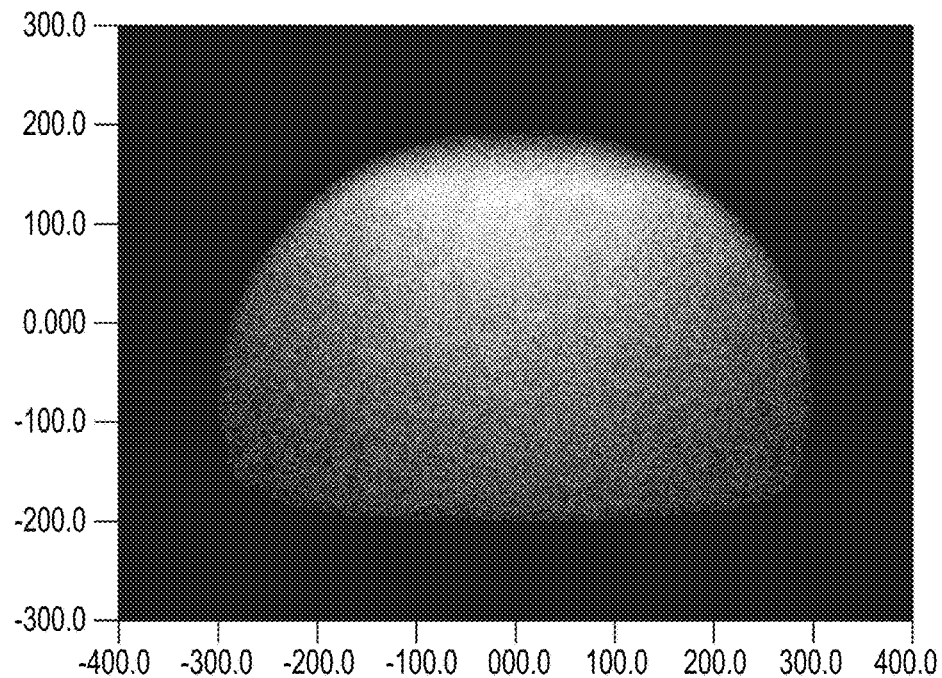
FIG. 8A is a diagram illustrating the distribution of light amount on the screen in the inspection system according to Numerical Example 1 of the embodiment in the diagnostic mode.
Figure 8B:
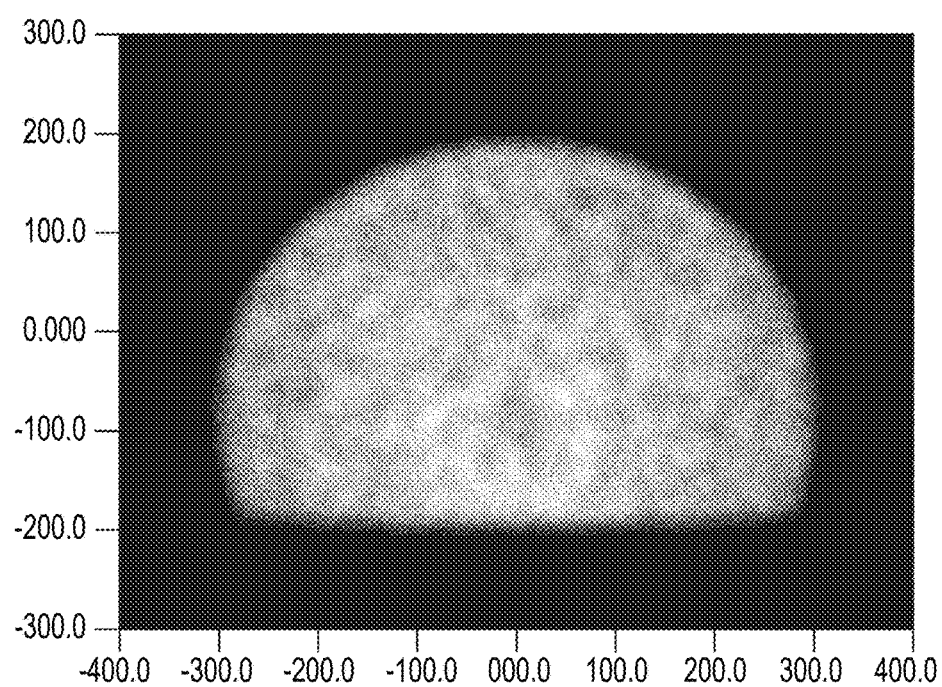
FIG. 8B is a diagram illustrating the distribution of light amount on the screen in the inspection system according to Numerical Example 1 of the embodiment in the preparation mode.

FIGS. 8A and 8B are diagrams illustrating the distributions of amount of light on the screen 3 in the inspection system 100 according to Numerical Example 1 of the embodiment in the diagnostic mode and the preparation mode, respectively, the light being video light to be incident on the eye point EP.

Here, in Numerical Example 1 of the embodiment, the coordinates of the middle point 34 on the incident surface (Fresnel surface) of the screen 3, the center of the exit surface of the projection lens of the projector 2, the center 51 of the reflection surface of the mirror 5, and the eye point EP during the diagnostic mode and the preparation mode are as listed in Tables 1 and 2 above, respectively.

In the inspection system 100 according to Numerical Example 1 of the embodiment, as illustrated in FIGS. 8A and 8B, the difference in brightness between the upper portion and the lower portion of the screen 3 is corrected particularly for the diagnostic mode as compared to the inspection system in the conventional example.

Figure 9A:
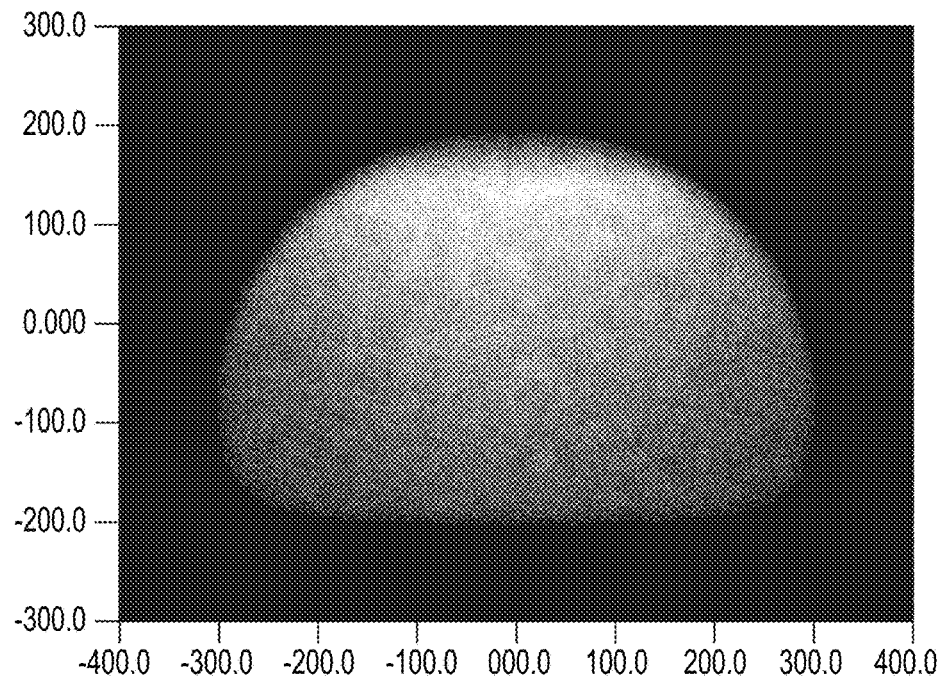
FIG. 9A is a diagram illustrating the distribution of light amount on the screen in the inspection system according to Numerical Example 2 of the embodiment in the diagnostic mode.
Figure 9B:
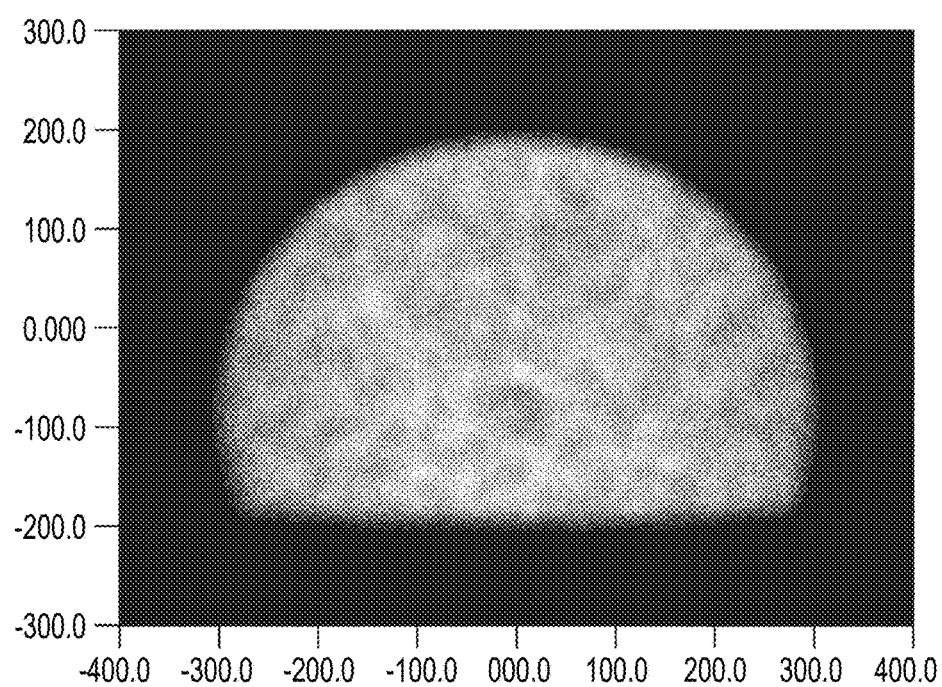
FIG. 9B is a diagram illustrating the distribution of light amount on the screen in the inspection system according to Numerical Example 2 of the embodiment in the preparation mode.

FIGS. 9A and 9B are diagrams illustrating the distributions of amount of light on the screen 3 in the inspection system 100 according to Numerical Example 2 of the embodiment in the diagnostic mode and the preparation mode, respectively, the light being video light to be incident on the eye point EP.

Figure 10:
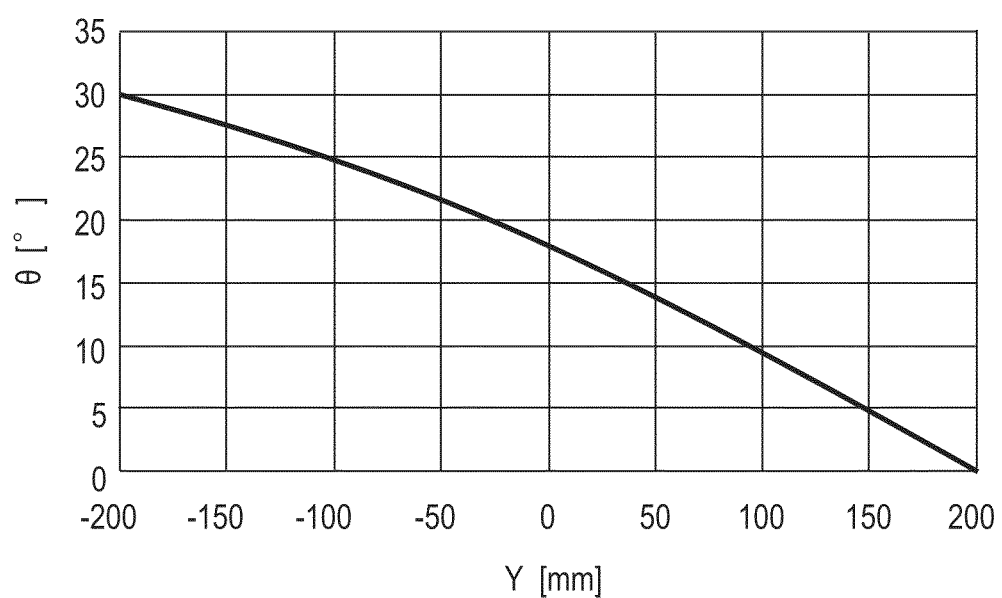
FIG. 10 is a diagram illustrating the distribution of the inclination angle of unit lenses on the screen according to Numerical Example 2 of the embodiment.

Here, in Numerical Example 2 of the embodiment, the inclination angle θ of the unit lenses in the Fresnel lens 31, which is formed on the screen 3, has a distribution as illustrated in FIG. 10.

Also, Table 3 below lists specification values of the inspection system 100 according to Numerical Example 2 of the embodiment.

As described in Table 3, the inspection system 100 according to Numerical Example 2 of the embodiment satisfies each conditional expression.

Here, in Numerical Example 2 of the embodiment, the coordinates of the middle point 34 on the incident surface (Fresnel surface) of the screen 3, the center of the exit surface of the projection lens of the projector 2, the center 51 of the reflection surface of the mirror 5, and the eye point EP during the diagnostic mode and the preparation mode are as listed in Tables 1 and 2 above, respectively.

In the inspection system 100 according to Numerical Example 2 of the embodiment, as illustrated in FIGS. 9A and 9B, the difference in brightness between the upper portion and the lower portion of the screen 3 is further corrected particularly for the diagnostic mode as compared to the inspection system in the conventional example.

Figure 11A:
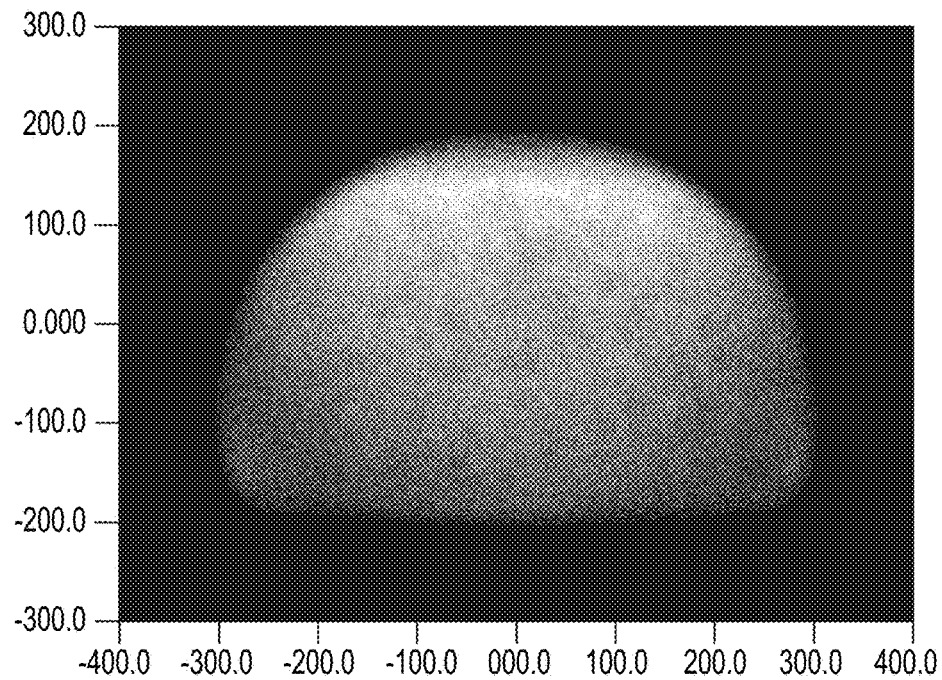
FIG. 11A is a diagram illustrating the distribution of light amount on a screen in an inspection system of a comparative example in the diagnostic mode.
Figure 11B:
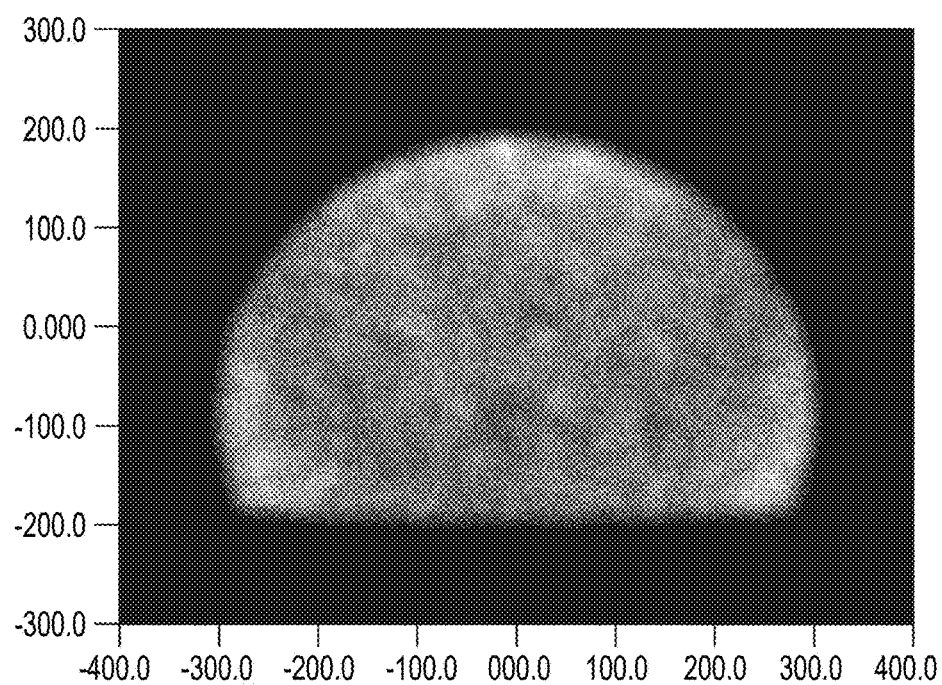
FIG. 11B is a diagram illustrating the distribution of light amount on the screen in the inspection system of the comparative example in the preparation mode.

FIGS. 11A and 11B are diagrams illustrating the distributions of amount of light on a screen 3 in an inspection system of a comparative example in the diagnostic mode and the preparation mode, respectively, the light being video light to be incident on the eye point EP.

Here, the inspection system of the comparative example has the same configuration as the inspection system 100 according to the embodiment and has the specification values listed in Table 3 below.

As described in Table 3, the inspection system of the comparative example does not satisfy the conditional expressions (4) and (5).

With the inspection system of the comparative example, as illustrated in FIGS. 11A and 11B, the difference in brightness between the upper portion and the lower portion of the screen 3 is corrected for the diagnostic mode as compared to the inspection system of the conventional example. For the preparation mode, however, the difference in brightness between a center portion and peripheral portions of the screen 3 is deteriorated.

TABLE 3

|  | Numerical Example 1 | Numerical Example 2 | Comparative Example |
|---|---|---|---|
| D1 | 400 mm | 400 mm | 400 mm |
| D2 | 200 mm | 200 mm | 200 mm |
| D3 | 360 mm | 360 mm | 360 mm |
| H1 | 470 mm | 470 mm | 470 mm |
| H2 | 430 mm | 430 mm | 430 mm |
| L1 | 1900 mm | 1900 mm | 1900 mm |
| L2 | 2900 mm | 2900 mm | 2900 mm |
| f | 2000 mm | 1200 mm | 600 mm |
| Conditional Expression (1) D2/D1 | 0.50 | 0.50 | 0.50 |
| Conditional Expression (2) H2/H1 | 0.91 | 0.91 | 0.91 |
| Conditional Expression (3) D3/D1 | 0.90 | 0.90 | 0.90 |
| Conditional Expression (4) f/L1 | 1.05 | 0.63 | 0.32 |
| Conditional Expression (5) f/L2 | 0.69 | 0.41 | 0.21 |

Although a preferred embodiment has been described above, the present invention is not limited the embodiment but can be modified and changed in various ways without departing from the gist of the invention.

According to the present invention, it is possible to provide an optical system to be installed in a projection system which is capable of allowing a patient to view a clear image in a diagnostic imaging apparatus.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2019-021195, filed Feb. 8, 2019, which is hereby incorporated by reference herein in its entirety.

What is claimed is:

1. An optical system comprising:
a Fresnel lens including a base material and a plurality of annular sections arranged around a center axis on a reference surface of the base material; and
a deflection element configured to deflect light from the Fresnel lens,
wherein, in a cross section including the center axis, an inclination angle of the annular sections to the reference surface changes asymmetrically between from a middle point of one and other ends of the Fresnel lens to the one end and from the middle point to the other end.

2. The optical system according to claim 1, wherein the following condition is satisfied:

$$0.2 < D2/D1 < 0.8,$$

where D1 is a distance from the one end to the other end along a first direction in the cross section, and D2 is a distance from the center axis to the middle point along the first direction.

3. The optical system according to claim 1, wherein the reference surface is a convex surface.

4. The optical system according to claim 1, wherein the Fresnel lens has a concave surface on an opposite side of the reference surface.

5. The optical system according to claim 1, wherein the center axis is located at the one end.

6. The optical system according to claim 1, wherein the Fresnel lens has a flat surface perpendicular to the cross section.

7. The optical system according to claim 1, wherein the plurality of annular sections are disposed on an opposite side of the deflection element with respect to the base material.

8. The optical system according to claim 1, wherein a deflection surface of the deflection element is perpendicular to the cross section.

9. The optical system according to claim 1, wherein the following condition is satisfied:

$$0.8 < D3/D1 < 1.2,$$

where D1 is a distance from the center axis to the other end along a first direction in the cross section, and D3 is a distance from a center of a deflection surface of the deflection element to the other end along the first direction.

10. A projection system comprising:
the optical system according to claim 1; and
a projection unit that projects an image onto the Fresnel lens.

11. The projection system according to claim 10, wherein in a first mode in which the deflection element is disposed between the Fresnel lens and a first focal point of the optical system along an optical path of light from the projection unit, the following condition is satisfied:

$$0.35 < f/L1 < 1.26,$$

where L1 is a distance from a projection lens of the projection unit to the middle point in a second direction perpendicular to the projection lens, and f is a focal length of the Fresnel lens.

12. The projection system according to claim 11, wherein in a second mode in which the deflection element is not disposed between the Fresnel lens and a second focal point of the optical system along an optical path of light from the projection unit, the following condition is satisfied:

$$0.24 < f/L2 < 0.83,$$

where L2 is a distance from the projection lens to the middle point in the second direction.

13. An inspection system comprising:
the projection system according to claim 10; and
a placement surface on which to place a subject.

14. The inspection system according to claim 13, wherein the Fresnel lens is held by the placement surface.

15. The inspection system according to claim 13, wherein the placement surface is movable.

* * * * *